US005629262A

United States Patent [19]
Auxier et al.

[11] Patent Number: 5,629,262
[45] Date of Patent: May 13, 1997

[54] METHOD FOR CONTROLLING GRASS WEEDS COMPRISING ADMINISTERING SYNERGISTIC AMOUNTS OF TWO CYCLOHEXENONE HERBICIDES

[75] Inventors: Barbara G. Auxier, Fuquay-Varina, N.C.; Wade W. Stewart, Brandon, Miss.; Neil P. Stapensea, Raleigh, N.C.

[73] Assignee: BASF Corporation, Mount Olive, N.J.

[21] Appl. No.: 548,992

[22] Filed: Oct. 27, 1995

[51] Int. Cl.$^6$ ................................................. A01N 33/24
[52] U.S. Cl. ............................................................ 504/148
[58] Field of Search ............................. 504/118, 130, 504/136, 138, 140, 148

[56] References Cited

U.S. PATENT DOCUMENTS 5,428,001   6/1995   Somers et al. ........................ 504/130

OTHER PUBLICATIONS

Synergistic Mixtures of Sethoxydim and Fluazifop on Annual Grass Weeds.

K. Neil Harker and P. Ashley O'Sullivan Weed Technology, 1991, vol. 5:310–316.

Secor et al. "Inhibition of Acetyl–CoA Carboxylase Activity by Haloxyfop and Tralkoxydim" *Plant Physiology*. 86:10–12. 1988.

*Primary Examiner*—S. Mark Clardy
*Attorney, Agent, or Firm*—Joanne P. Will

[57] ABSTRACT

A method for controlling grass weeds in growing crops comprising administering two acetyl coA carboxylase inhibitors at synergistically effective amounts, i.e., sethoxydim, clethodim, and caloxydim.

18 Claims, No Drawings

METHOD FOR CONTROLLING GRASS WEEDS COMPRISING ADMINISTERING SYNERGISTIC AMOUNTS OF TWO CYCLOHEXENONE HERBICIDES

FIELD OF THE INVENTION

The present invention relates to a method for controlling grass weeds in growing crops comprising administering synergistically effective amounts of two acetyl coA carboxylase inhibitors.

BACKGROUND

The effective, economical, and environmentally sound control of grass weeds in growing crops is a major problem for farmers. Weeds cost farmers billions of dollars annually in crop losses and in the expense of keeping the weeds under control. The losses caused by weeds in agricultural production environments include decrease in crop yield, reduced crop quality, increased irrigation costs, increased harvesting costs, decreased land value, injury to livestock, and crop damage from insects and diseases harbored by these weeds.

Those skilled in the art are continuously attempting to find better methods to control grass weeds in growing crops. One such method is the administration of the acetyl coA carboxylase inhibitor herbicides such as sethoxydim, clethodim, quizalofop-p-ethyl, fluazifop-p-butyl, fenoxaprop-p-ethyl and caloxydim (developmental cyclohexenone). See, Herbicide Handbook—Weed Science Society of America—Seventh Edition, 1994. Further, the art teaches the administration of these herbicides alone or in conjunction with other herbicides having a different mechanism of action other than acetyl coA carboxylase inhibition. Specifically, the following publications all disclose that sethoxydim or clethodim are effective at standard lethal doses in controlling grass weeds in growing crops: *Growth Stage Comparison of Postemergence Herbicides on Three Grass Species*, Snipes, C. E.; Lantham, D. J.; Bulletin—Mississippi Agricultural and Forestry Experiment Station, (1994), No. 1015, pp. 7; *The Effect of Giant Foxtail (Setaria faberi) Plant Height on Control With Six Postemergence Herbicides*, Krausz, R. F.; Kapusta, G.; Matthews, J. L.; Weed Technology, (1993) Vol. 7, No. 2, pp. 491–491; *Efficacy and Economics of Common Bermuda Grass (Cynodon dactylon) Control in Peanut (Arachis hypogaea)*; Wilicut, J. W.; Peanut Science, (1991) Vol. 18, No. 2, pp. 106–109; *Johnsongrass (Sorghum halepense) Control in Soybeans (Glycine max) With Postemergence Herbicides*; Johnson, W. G.; Frans, R. E.; Weed Technology, (1991) Vol. 5, No. 1, pp. 87–91; *Herbicides for Control of Mercer Grass (Paspalum distichum) in Asparagus*; Rahman, A.; Sanders, P.; Asparagus Research Newsletter, (1991) Vol. 8, No. 2, pp. 20–23; *Control of Texas Panicum (Panicum texanum) and Southern Crabgrass (Digitaria cillaris) in Peanuts (Arachis hypogaea) with Postemergence Herbicides*; Grichar, W. J.; Peanut Science, (1991) Vol. 18, No. 1, pp. 6–8; *Wild-Proso Millet (Panicum miliaceum) Control in Soyabeans (Glycine max) with Postemergence Herbicides*; Harvey, R. G.; Porter, D. J.; Weed Technology, (1990) Vol. 4, No. 2, pp. 420–424; *Herbicides for the Control of Mercer Grass (Paspalum distichum) in Asparagus*; Rahman, A.; Sanders, P.; MAF Technology North, Ruarkura Agricultural Centre, Private Bag, Hamilton, New Zealand. (1990) pp. 48–51; *Grass Control Herbicides in Soybean*; Skrzypczak, G. A.; Wright, D. L.; Proceedings, Soil and Crop Science Society of Florida, (1988) Vol. 47, pp. 150–157. However, their use together at synergistically effective amounts is not disclosed.

Additionally, the synergistically effective administration of two herbicides having different mechanisms of action is disclosed. See, U.S. Pat. No. 5,108,488 assigned to Valent that discloses the postemergent administration of a composition comprising synergistically effective amounts of clethodim and flumioxazin, a primarily broadleaf weed herbicide; U.S. Pat. No. 5,238,901 assigned to Sumitomo that discloses the preemergent application of a composition comprising synergistically effective amounts of flumioxazin, a primarily broadleaf weed herbicide, and alachlor; U.S. Pat. No. 4,517,009 assigned to FBC, Limited that discloses the postemergent administration of a composition comprising synergistically effective amounts of benazolin and acifluorfen; U.S. Pat. No. 4,378,990 assigned to Schering AG that discloses the postemergent administration of a composition comprising synergistically effective amounts of 5-(N-phenyl carbamoylamino) 1,2,3-thiadiazole and a phenyl ether; and U.S. Pat. No. 5,047,080 assigned to Sumitomo that discloses the postemergent administration of a composition comprising a synergistically effective amount of flumioxazin, a primarily broad leaf weed herbicide, and sethoxydim or alloxydim.

The existing art also teaches that two acetyl coA carboxylase inhibiting herbicides can be effective on grass weeds when blended together at their full lethal dosage rates. An example of this is FUSION®, which is a premix of fluazifop-p-butyl and fenoxaprop-p-ethyl.

However, the art does not teach or suggest that two herbicides, having the same mechanism of action, i.e., acetyl coA carboxylase inhibiting herbicides effective on grass weeds, can be blended together in sub-lethal amounts in a tank mix, and applied at these sub-lethal amounts to provide effective control of grass weeds in growing crops. Thus, Applicants' discovery that sub-lethal amounts of two acetyl coA carboxylase inhibiting herbicides provide effective grass weed control is an unexpected advance in the herbicide art.

SUMMARY

A method for controlling grass weeds in growing crops comprising administering two acetyl coA carboxylase inhibitors at synergistically effective amounts.

DEFINITIONS AND USAGES OF TERMS

The term "grass weeds" as used herein includes, but is not limited to, crabgrass (*Digitaria sanguinalis*), foxtails (*Setaria* species), goosegrass (*Eleusine indica*), Texas panicum (*Panicum texanum*), rhizome johnsongrass (*Sorghum halepense*) , common bermudagrass (*Cynodon dactylon*), barnyardgrass (*Echinochloa crus-galli*), green foxtail (*Setaria viridis*), giant foxtail (*Setaria faberi*), yellow foxtail (*Setaria glauca*), quackgrass (*Agropyron repens*), and shattercane (*Sorghum bicolor*).

The term "sub-lethal dose range", as used herein, refers to the dose range of a single herbicide at which the grass weeds are suppressed or only partially destroyed.

The term "effective lethal dose" or "lethal dose", as used herein, refers to the dose range of a single herbicide at which the grass weeds are controlled 80% or greater. The effective lethal dose range can vary with climatic conditions.

The term "synergistically effective amount", as used herein, refers to the sub-lethal doses of two herbicides blended together and administered conjointly which then provides a lethal grass weed killing effect of 80% or greater; 80% or greater being the commercially accepted standard for weed control. In other words, "synergism" means the combined action of two or more agents blended together and administered conjointly that is greater than the sum of their individual effects.

The term "acetyl coA carboxylase inhibitor herbicide", as used herein, refers to a herbicide whose mechanism of action is the inhibition of the acetyl coA carboxylase enzyme which is the catalyst for fatty acid synthesis (an important step in cell membrane biosynthesis).

DETAILED DESCRIPTION

A method for controlling grass weeds in growing crops comprising administering two acetyl coA carboxylase inhibitors at synergistically effective amounts.

COMPOUNDS USEFUL IN THE PRACTICE OF THE PRESENT INVENTION

The acetyl coA inhibitors useful in the practice of the present invention include, but are not limited to, CLETHODIM, (E,E)-(±)-2-[1-[[(3-chloro-2-propenyl)oxy]imino]propyl]-5-[2-(ethylthio)propyl]-3-hydroxy-2-cyclohexen-1-one (CAS number99129-21-2); Clethodim can be applied post emergence (POST) at 0.105–0.28 kg ai/ha (0.094–0.25 lb ai/A) in cotton and soybeans for control of many annual and perennial grasses. An oil adjuvant is needed for maximum efficacy. Clethodim has no activity against broadleaf weeds and sedges; FENOXAPROP-P-ETHYL, (±)-2-[4-[6-chloro-2-benzoxazolyl)oxy]phenoxy]propionate(CAS number 66441-23-4); Fenoxaprop-P-ethyl can be applied POST at 37.5–111 g ai/ha (0.0335–0.0995 lb ai/A) in soybeans, POST at 0.04–0.39 kg ai/ha (0.03–0.35 lb ai/A) in turf, POST at 32.8–91.5 g ai/ha (0.0293–0.0817 lb ai/A) in wheat, and POST at 70.4–93.8 g ai/ha (0.0628–0.0838 lb ai/A) in conservation reserve (set aside) land; FLUAZIFOP-P-BUTYL,(R)-2-[4-[[5-(trifluoromethyl)-2-pyridinyl]oxy]phenoxy]propanoate (CAS number 69335-91-7); Fluazifop-P-butyl can be applied POST at 0.053–0.21 kg ai/ha (0.047–0.188 lb ai/A) in cotton, soybeans, stone fruits, asparagus, carrots, garlic, coffee, endive, pecans, rhubarb, and tabasco peppers. It controls most annual and perennial grass weeds including barnyardgrass, crabgrass spp., downy brome, Panicum spp., foxtail spp., volunteer cereals, shattercane, quackgrass, and johnsongrass. Fluazifop-P-butyl has essentially no activity on broadleaf species. An oil adjuvant or nonionic surfactant is required for maximum efficacy; QUIZALOFOP-P-ETHYL, (R)-2-[4-[(6-chloro-2-quinoxalinyl)oxy]phenoxy]propionate (CAS number 76578-14-8); Quizalofop-P-ethyl provides POST control of annual and perennial grass weeds in soybeans and non-crop areas. It can be applied POST at 35–84 g ai/ha (0.031–0.075 lb. ai/A) in soy crop areas, and POST in a spray-to-wet application at 0.75% v/v for spot treatment in soybeans. Quizalofop-P-ethyl controls nearly all weedy annual grasses and most perennial grass weeds including johnsongrass, bermudagrass, quackgrass, and wirestem muhly. A nonionic surfactant or oil adjuvant is required for maximum efficacy; SETHOXYDIM, 2-[1-(ethoxyimino)butyl]-5-[2-(ethylthio)propyl]-3-hydroxy-2-cyclohexen-1-one (CAS number 74051-80-2); Sethoxydim controls annual and perennial grasses in several broadleaf crops. It can be applied as follows: POST at 112–448 g ai/ha (0.1–0.4 lb ai/A) in soybeans and peanuts; POST at 112–560 g ai/ha (0.1–0.5 lb ai/A) in alfalfa, sugarbeets, sunflowers, and cotton; POST at 112–560 g ai/ha (0.1–0.5 lb ai/A) in flax; as a foliar-applied preplant burndown at 112 g ai/ha of no-till soybeans; POST at 336–560 g ai/ha (0.3–0.5 lb. ai/A) in many ornamental trees, shrubs, flowers, and ground covers; POST at 1–1.5% v/v as a spray-to wet application for spot spraying in soybeans and ornamentals. An oil adjuvant or nonionic surfactant is required for maximum efficacy. See, Herbicide Handbook, Weed Science Society of America, 7th Edition, 1994 and The Pesticide Manual, 10th Edition, Ed. Clive Tomlin, Crop Protection Publications, British Crop Protection Council, all incorporated by reference herein. CALOXYDIM, 2-[1-((3-chloro-2-(E)-propen-1-yl)oximino)propyl-3-hydroxy-5-tetrahydropyran-4-yl]-2-cyclohexene-1-one-(tetrahydropyran) (CAS number 149979-41-9), applied POST at 0.05–0.125 lbs. ai/acre.

Preparation and Application of the Synergistically Effective Herbicidal Blends The synergistically effective compositions useful in the practice of the present invention are prepared by tank mixing sub-lethal amounts of two acetyl coA carboxylase inhibiting herbicides according to methods known to those skilled in the art. Synergistically effective compositions useful in the practice of the present invention can be prepared accordingly: In a mixing tank, fill tank ⅔ with water, add 1 qt./acre of a crop oil concentrate ("COC"), add each of the 2 acetyl coA carboxylase inhibitors at the synergistically effective (sub-lethal) doses, agitate and fill tank to volume. Further, those skilled in the art understand that other tank mix additives may be added, including but not limited to surfactants, fertilizers and sequestrants. Suitable surfactants include, but are not limited to, nonionic surfactants, anionic surfactants, cationic surfactants and amphoteric surfactants. Suitable nonionic surfactants include:

a) Polyoxyethylene or polyoxypropylene condensates of aliphatic carboxylic acids which are linear or branched-chain and unsaturated or saturated.

b) Polyoxyalkylene (polyoxyethylene or polyoxypropylene) condensates of aliphatic alcohols which are linear or branched-chain and unsaturated or saturated. Industrol DW5® available from BASF Corporation is a preferred condensate of an aliphatic alcohol type surfactant.

c) Polyoxyalkylene oxide block copolymers (polyoxyethylene or polyoxypropylene condensates of alkyl phenols, which are linear or branched-chain, unsaturated or saturated.) Polyalkylene oxide block copolymers are sold under the tradename "Pluronic"® made by the BASF Corporation, Mt. Olive, N.J.

Suitable anionic surfactants include water soluble salts of higher fatty acids. Useful anionic surfactants include sodium and potassium alkyl sulfates; sodium and potassium alkylbenzenesulfonates; sodium alkyl glyceryl ether sulfonates; water-soluble salts of esters of alpha-sulfonated fatty acids; alkali metal salts of $C_{11-13}$ alkylbenzene sulfonates; $C_{12-18}$ alkyl sulfates; $C_{12-18}$ alkyl linear polyethoxy sulfates.

Suitable cationic surfactants include compounds characterized by one or more organic hydrophobic groups in the cation and generally by a quarternary nitrogen associated with the acid radical such as alkyl dimethyl benzyl ammonium chloride;

Suitable amphoteric surfactants include aliphatic derivatives of heterocyclic secondary and tertiary amines.

Finally, *Surfactant Science Series*, edited by Martin J. Schick, provides a detailed description of useful surfactants and is incorporated by reference herein.

Synergistically effective doses are preferably ¹⁄₂₀ to ⅓ of the effective lethal dose for controlling grass weeds, more preferably ¹⁄₁₀ to ⅓ of the effective lethal dose; most preferably ⅕ to ⅓ of the effective lethal dose. In other words, synergistically effective doses are the sub-lethal doses of two acetyl coA carboxylase inhibiting herbicides blended together and administered conjointly. This results in greatly enhanced grass weed control over that observed from sub-lethal doses of either compound applied alone. Specifically, the synergistically effective amounts of sethoxydim and clethodim can be applied together from a tank mix formulation using application methods known to those skilled in the art, such as spraying.

The sethoxydim and clethodim formulations can be applied at the following representative, but not limiting, sub-lethal rates:

sethoxydim, 0.02 to 0.13 lbs. ai/acre (1/20 to 1/3 lethal dose of 0.4 lbs. ai/acre) plus clethodim, 0.0125 to 0.08 lbs. ai/acre (1/20 to 1/3 of the lethal dosage of 0.25 lbs. ai/acre)

sethoxydim, 0.04 to 0.13 lbs. ai/acre (1/10 to 1/3 lethal dose of 0.4 lbs. ai/acre) plus clethodim, 0.025 to 0.08 lbs. ai/acre (1/10 to 1/3 the lethal dosage of 0.25 lbs. ai/acre) or sethoxydim, 0.08 to 0.13 lbs. ai/acre (1/5 to 1/3 lethal dose of 0.4 lbs. ai/acre) plus clethodim, 0.05 to 0.08 lbs. ai/acre (1/5 to 1/3 lethal dosage of 0.25 lbs. ai/acre)

Further, either sethoxydim or clethodim may be mixed with other acetyl coA carboxylase inhibitors such as caloxydim; fenoxaprop-p-ethyl; fluazifop-p-butyl; and quizalofop-p-ethyl. Representative sethoxydim or clethodim plus other acetyl coA carboxylase inhibitor applications include:

Synergistically effective amounts of sethoxydim or clethodim, as described hereinabove, plus caloxydim, 0.006 to 0.04 lbs. ai/acre (1/20 to 1/3 of the lethal dose of 0.125 lbs. ai/acre) or caloxydim, 0.0125 to 0.04 lbs. ai/acre (1/10 to 1/3 of the lethal dose of 0.125 lbs. ai/acre) or caloxydim, 0.025 to 0.04 lbs. ai/acre (1/5 to 1/3 of the lethal dose of 0.125 lbs. ai/acre) or Synergistically effective amounts of sethoxydim or clethodim, as described hereinabove, plus fenoxaprop-p-ethyl, 0.005 to 0.033 lbs. ai/acre (1/20 to 1/3 of the lethal dose of 0.1 lbs. ai/acre) or fenoxaprop-p-ethyl, 0.01 to 0.033 lbs. ai/acre (1/10 to 1/3 of the lethal dose of 0.1 lbs. ai/acre) or fenoxaprop-p-ethyl, 0.02 to 0.033 lbs. ai/acre (1/5 to 1/3 of the lethal dose of 0.1 lbs. ai/acre) or Synergistically effective amounts of sethoxydim or clethodim, as described hereinabove, plus fluazifop-p-butyl, 0.01 to 0.063 lbs. ai/acre (1/20 to 1/3 of the lethal dose of 0.19 lbs. ai/acre) or fluazifop-p-butyl, 0.019 to 0.063 lbs. ai/acre (1/10 to 1/3 of the lethal dose of 0.19 lbs. ai/acre) or fluazifop-p-butyl, 0.038 to 0.063 lbs. ai/acre (1/5 to 1/3 of the lethal dose of 0.19 lbs. ai/acre) or Synergistically effective amounts of sethoxydim or clethodim, as described hereinabove, plus quizalofop-p-ethyl, 0.004 to 0.025 lbs. ai/acre (1/20 to 1/3 of the lethal dose of 0.075 lbs. ai/acre) or quizalofop-p-ethyl, 0.008 to 0.025 lbs. ai/acre (1/10 to 1/3 of the lethal dose of 0.075 lbs. ai/acre) or quizalofop-p-ethyl, 0.016 to 0.025 lbs. ai/acre (1/5 to 1/3 of the lethal dose of 0.075 lbs. ai/acre).

The synergistic effectiveness of a tank mix of sublethal doses of sethoxydim and clethodim on grass weeds is illustrated in Tables 1, 2, 3 and 4.

TABLE 1

Southern Field Trials (Average of 9 trials)

| Treatment | Rate (lbs. ai/acre) | Expected[2] % Control | Actual % Control (SORHAR)[1] |
|---|---|---|---|
| Poast Plus (Sethoxydim) | 0.19 (sub-lethal dose) | — | 77 |
| Select (Clethodim) | 0.125 (lethal dose) | — | 92 |
| Poast Plus | 0.06 (sub-lethal dose) | 25.4 | — |
| Select | 0.03 (sub-lethal dose) | 23.0 | — |
| Poast Plus & Select | 0.06 ± 0.03 | 48.4 | 83 |

[1]SORHAR = rhizome johnsongrass % control refers to visual reduction of weed biomass (46 days after treatment (DAT)).
[2]Expected control values were mathematically derived by taking 33% of the actual % control results since only 33% of the normal product use rates are needed to achieve the synergistic effect.
All treatments were applied with 1.25% crop oil concentrate (COC)
Spray volume = 10 gallons/acre (GPA) (1.25% of 10 GPA = 1 pt/acre COC).

TABLE 2

Greenhouse Trial

| Treatment | Rate (lb ai/A) | % SORVU Control Expected | Actual |
|---|---|---|---|
| Poast Plus (Sethoxydim) | 0.064 (sub-lethal green house dose) | | 78 |
| Select (Clethodim) | 0.032 (lethal green house dose) | | 88 |
| Poast Plus | 0.016 (sub-lethal dose) | | 58 |
| Select | 0.004 (sub-lethal dose) | | 5 |
| Poast Plus & Select | 0.016 ± 0.004 | 63 | 80 |

SORVU = Sorghum vulgare, Shattercane
% Control evaluated 14 (days after treatment (DAT))
All Treatments applied with 1.25% v/v COC (Atplus 411 F available from ICI, Inc., Wilmington, Delaware)
Spray Volume = 20 gallons/acre (GPA) (1.25% of 20 GPA = 1 qt/A COC)

The data in Table 2 was obtained from a greenhouse trial where all growing and climatic conditions are optimal. Thus, much lower dosage rates than those needed in the field can produce the lethal as well as the synergistic effect.

TABLE 3

Field Test Site Trials

| Treatment | Rate (lb ai/A) | % DIGSA Control Expected | Actual |
|---|---|---|---|
| Poast Plus (Sethoxydim) | 0.125 (lethal dose) | | 100 |
| Select (Clethodim) | 0.061 (lethal dose) | | 100 |
| Poast Plus | 0.031 (sub-lethal dose) | | 10 |
| Select | 0.020 (sub-lethal dose) | | 18 |
| Poast Plus & Select | 0.031 ± 0.020 | 28 | 82 |

TABLE 3-continued

| | Field Test Site Trials | | |
|---|---|---|---|
| | Rate | % DIGSA Control | |
| Treatment | (lb ai/A) | Expected | Actual |

DIGSA = *Digitaria sanguinalis*, large crabgrass
% Control evaluated 26–27 DAT
All Treatments applied with 1.25% v/v COC (Atplus 411 F available from ICI, Inc., Wilmington, Delaware)
Spray Volume = 10 GPA (1.25% of 10 GPA = 1 qt/A COC)

The data in Table 3 was obtained from an actual outdoor field trial where climatic conditions are not always optimal and readily controlled. Nevertheless, the synergistic effectiveness of the two acetyl coA carboxylase inhibitors is clearly illustrated.

TABLE 4

| | Greenhouse Trial | | |
|---|---|---|---|
| | Rate | % SORHAR Control | |
| Treatment | (lbs. ai/acre) | Expected | Actual |
| Poast Plus (Sethoxydim) | 0.19 (lethal green house dose) | — | 93 |
| Select (Clethodim) | 0.09 (lethal green house dose) | — | 100 |
| Poast Plus | 0.062 (⅓ lethal dose) | — | 35 |
| Select | 0.031 (⅓ lethal dose) | — | 33 |
| Poast Plus & Select | 0.062 ± 0.031 | 68 | 100 |

% Control evaluated 29 DAT (days after treatment)
All treatments applied with 1.25% v/v COC.
Spray Volume = 10 GPA (1.25% v/v of 10 GPA = 1 pt/A COC)

What is claimed:

1. A method for controlling grass weeds in growing crops comprising administering two cyclohexanedione herbicides at synergistically effective amounts.

2. A method for controlling grass weeds in growing crops comprising administering two cyclohexanedione herbicides at sub-lethal amounts.

3. A method for controlling grass weeds in growing crops comprising administering two acetyl co A carboxylase inhibitors at synergistically effective amounts, wherein further, said two acetyl co A carboxylase inhibitors are sethoxydim and clethodim.

4. A method according to claim 3, wherein sethoxydim is administered at a rate of 0.02 to 0.13 lbs. ai/acre and clethodim is administered at a rate of 0.0125 to 0.08 lbs. ai/acre.

5. A method according to claim 3, wherein sethoxydim is administered at a rate of 0.04 to 0.13 lbs. ai/acre and clethodim is administered at a rate of 0.025 to 0.08 lbs. ai/acre.

6. A method according to claim 3, wherein sethoxydim is administered at a rate of 0.08 to 0.13 lbs. ai/acre and clethodim is administered at a rate of 0.05 to 0.08 lbs. ai/acre.

7. A method for controlling grass weeds in growing crops comprising administering two acetyl co A carboxylase inhibitors at sub-lethal amounts, wherein further, said two acetyl co A carboxylase inhibitors are sethoxydim and clethodim.

8. A method according to claim 7, wherein sethoxydim is administered at a rate of 0.02 to 0.13 lbs. ai/acre and clethodim is administered at a rate of 0.0125 to 0.08 lbs. ai/acre.

9. A method according to claim 7, wherein sethoxydim is administered at a rate of 0.04 to 0.13 lbs. ai/acre and clethodim is administered at a rate of 0.025 to 0.08 lbs. ai/acre.

10. A method according to claim 7, wherein sethoxydim is administered at a rate of 0.08 to 0.13 lbs. ai/acre and clethodim is administered at a rate of 0.05 to 0.08 lbs. ai/acre.

11. A method for controlling grass weeds in growing crops comprising administering two acetyl co A carboxylase inhibitors at synergistically effective amounts, wherein further, said two acetyl co A carboxylase inhibitors are sethoxydim and caloxydim.

12. A method according to claim 11, wherein sethoxydim is administered at a rate of 0.04 to 0.13 lbs. ai/acre and caloxydim is administered at a rate of 0.0125 to 0.04 lbs. ai/acre.

13. A method for controlling grass weeds in growing crops comprising administering two acetyl co A carboxylase inhibitors at sub-lethal amounts, wherein further, said two acetyl co A carboxylase inhibitors are sethoxydim and caloxydim.

14. A method according to claim 13, wherein sethoxydim is administered at a rate of 0.04 to 0.13 lbs. ai/acre and caloxydim is administered at a rate of 0.0125 to 0.04 lbs. ai/acre.

15. A method for controlling grass weeds in growing crops comprising administering two acetyl co A carboxylase inhibitors at synergistically effective amounts, wherein further, said two acetyl co A carboxylase inhibitors are clethodim and caloxydim.

16. A method according to claim 15, wherein clethodim is administered at a rate of 0.025 to 0.08 lbs. ai/acre and caloxydim is administered at a rate of 0.0125 to 0.04 lbs. ai/acre.

17. A method for controlling grass weeds in growing crops comprising administering two acetyl co A carboxylase inhibitors at sub-lethal amounts, wherein further, said two acetyl co A carboxylase inhibitors are clethodim and caloxydim.

18. A method according to claim 17, wherein clethodim is administered at a rate of 0.025 to 0.04 lbs. ai/acre and caloxydim is administered at a rate of 0.0125 to 0.04 lbs. ai/acre.

* * * * *